United States Patent
McGrath et al.

(10) Patent No.: US 9,775,505 B2
(45) Date of Patent: Oct. 3, 2017

(54) LARYNGOSCOPE INSERTION SECTION STRUCTURE

(75) Inventors: Matthew John Ross McGrath, Edinburgh (GB); Peter Douglas Colin Inglis, Edinburgh (GB)

(73) Assignee: AIRCRAFT MEDICAL LIMITED, Edinburgh (GB)

(*) Notice: Subject to any disclaimer, the term of this patent is extended or adjusted under 35 U.S.C. 154(b) by 820 days.

(21) Appl. No.: 13/697,701

(22) PCT Filed: May 13, 2011

(86) PCT No.: PCT/GB2011/050924
§ 371 (c)(1),
(2), (4) Date: Nov. 13, 2012

(87) PCT Pub. No.: WO2011/141751
PCT Pub. Date: Nov. 17, 2011

(65) Prior Publication Data
US 2013/0060089 A1    Mar. 7, 2013

(30) Foreign Application Priority Data

May 13, 2010  (GB) .................................. 1008023.2
Oct. 13, 2010  (GB) .................................. 1017294.8
Oct. 26, 2010  (GB) .................................. 1018086.7

(51) Int. Cl.
*A61B 1/267* (2006.01)

(52) U.S. Cl.
CPC .................................. *A61B 1/267* (2013.01)

(58) Field of Classification Search
CPC combination set(s) only.
See application file for complete search history.

(56) References Cited

U.S. PATENT DOCUMENTS 3,595,222 A * 7/1971 Vellacott ................ A61B 1/267
                                                              362/205
3,930,507 A * 1/1976 Berman .................... 128/207.14
(Continued)

FOREIGN PATENT DOCUMENTS

CN    2158237 Y    3/1994
EP    1 820 439    8/2007
(Continued)

OTHER PUBLICATIONS

International Search Report for PCT/GB2011/050924, mailed Dec. 19, 2011, 6 pages.

*Primary Examiner* — Jan Christopher Merene
(74) *Attorney, Agent, or Firm* — Fletcher Yoder PC

(57) ABSTRACT

Disclosed is a laryngoscope insertion section having a curved superior surface and a curved inferior surface, and a channel extending from the proximal end the channel having an inferior internal surface with a greater curvature than the curvature of the inferior surface. The insertion section is compatible with laryngoscope hardware optimized for indirect viewing, yet enables direct viewing. Additionally, the distance between the inferior and superior surfaces is at a maximum within the intermediate portion, and enables the dimensions of the proximal and distal portions to be minimized. Thus, the intermediate portion, which is located in the patient's oral cavity in use, is provided with greatest depth and therefore strength where the greatest forces are received, whereas the distal and proximal portions are of reduced dimensions to as to minimize trauma to the patient's airway and mouth areas, respectively, in use. Further structural features providing the insertion section with improved strength, with a minimum of material and size, are also disclosed.

33 Claims, 7 Drawing Sheets

(56) References Cited

U.S. PATENT DOCUMENTS

| | | | |
|---|---|---|---|
| 3,986,854 A * | 10/1976 | Scrivo et al. | 65/410 |
| 4,565,187 A * | 1/1986 | Soloway | 600/193 |
| 4,570,614 A | 2/1986 | Bauman | |
| 5,163,431 A * | 11/1992 | Griep | 600/435 |
| 5,716,329 A * | 2/1998 | Dieter | 600/210 |
| 5,913,816 A * | 6/1999 | Sanders et al. | 600/120 |
| 6,102,851 A | 8/2000 | Mellin | |
| 2004/0220452 A1* | 11/2004 | Shalman | 600/157 |
| 2005/0240081 A1 | 10/2005 | Eliachar | |
| 2007/0197873 A1 | 8/2007 | Birnkrant | |
| 2008/0045801 A1 | 2/2008 | Shalman et al. | |
| 2010/0036204 A1 | 2/2010 | Anders | |
| 2010/0256451 A1* | 10/2010 | McGrath et al. | 600/185 |

FOREIGN PATENT DOCUMENTS

| | | |
|---|---|---|
| EP | 1820439 | 8/2007 |
| EP | 2 151 185 | 2/2010 |
| EP | 2151185 | 2/2010 |
| GB | 2 102 679 A | 2/1983 |
| GB | 2 385 793 | 9/2003 |
| GB | 2385793 | 9/2003 |
| JP | 2006-525058 | 11/2006 |
| WO | 8301373 | 4/1983 |
| WO | WO 83/01373 | 4/1983 |
| WO | 02/03851 | 1/2002 |
| WO | 02/100238 | 12/2002 |
| WO | 02100238 | 12/2002 |
| WO | WO 02/100238 | 12/2002 |
| WO | 2004/096032 | 11/2004 |
| WO | 2008/020296 | 2/2008 |
| WO | 2009/027669 | 3/2009 |
| WO | WO 2010/019597 A2 | 2/2010 |

* cited by examiner

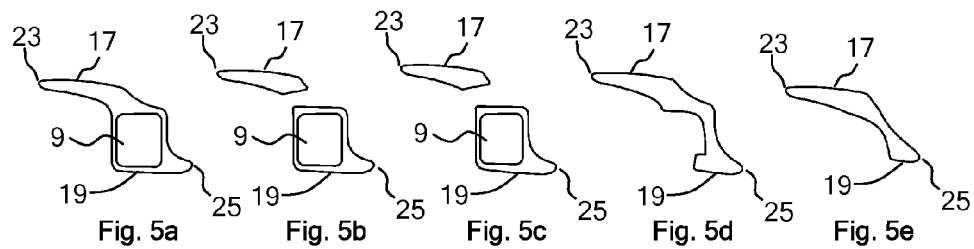
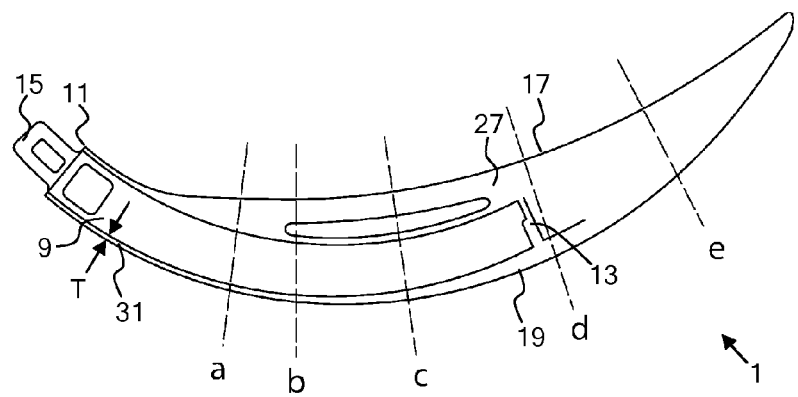
Fig. 4
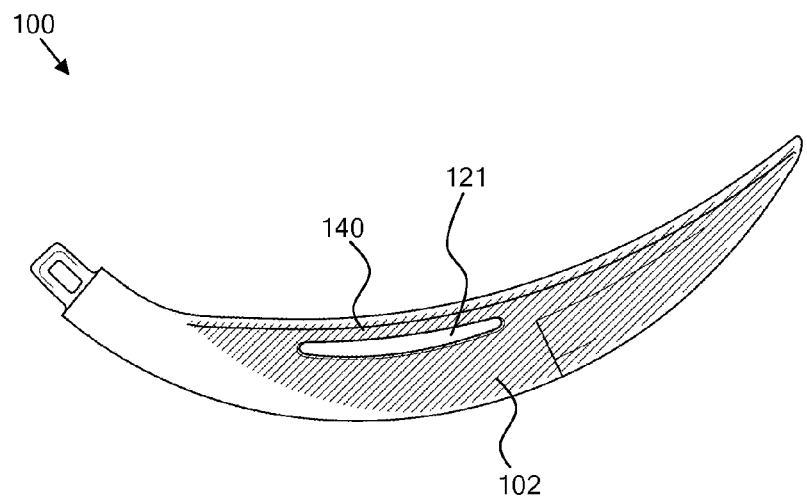
Fig. 6

LARYNGOSCOPE INSERTION SECTION STRUCTURE

This application is the U.S. national phase of International Application No. PCT/GB2011/050924, filed 13 May 2011, which designated the U.S. and claims priority to GB Application No. 1008023.2, filed 13 May 2010; GB Application No. 1017294.8, filed 13 Oct. 2010, and GB Application No. 1018086.7, filed 26 Oct. 2010, the entire contents of each of which are hereby incorporated by reference.

FIELD OF THE INVENTION

The invention relates to the field of laryngoscope insertion sections and in particular to single or limited use laryngoscope insertion sections adapted to receive laryngoscope hardware or integral to single or limited use laryngoscopes.

BACKGROUND TO THE INVENTION

Laryngoscopes are medical devices in common use in oral and tracheal medical procedures, and may be used to obtain view of the glottis or larynx, or to manipulate the tongue, glottis or larynx in order to facilitate insertion of endotracheal tubes or other instruments such as endoscopes, which may be separate pieces of equipment, or may be integral to a laryngoscope.

A laryngoscope typically comprises an insertion section, which is an elongate section which extends towards and into a patient's oral cavity during a medical procedure such as intubation. A laryngoscope insertion section is typically connected to (integrally or removably) to a body, which usually functions as a handle or is demountably attachable to an insertion section in which the handle and the part which extend into a patient's oral cavity in use are integrated.

Some known laryngoscope insertion sections, such as Miller or Wisconsin insertion sections, are substantially flat. However, the insertion section of a laryngoscope is more commonly bent to better enter through a patient's oropharynx towards their larynx. Some known insertion sections include first and second straight portions, with a bend therebetween, or are curved, at least in part.

Within this specification and the appended claims, the inferior surface is the surface of an insertion section which faces the patient's tongue in use. Accordingly, the inferior surface is not defined by ancillary features of a laryngoscope insertion section, such as means for mechanically securing a proximal portion to a laryngoscope body, tube guiding elements extending laterally from the insertion section and/ or any surfaces of an endotracheal tube secured to a tube guide.

The opposite surface is referred to as the superior surface. Words such as inferior, inferiorly, superior and superiorly are used in corresponding senses. A superior-inferior axis is a virtual axis extending parallel to the superior and inferior directions.

The words distal and distally refer to being towards the end of the insertion section which extends towards a patient's trachea in use and the words proximal and proximally refer to being towards the person carrying out the medical procedure, in use.

By depth, or thickness, we mean the distance, at any point along the length of the laryngoscope insertion section, between the inferior surface and the superior surface.

By width we mean the distance across the laryngoscope insertion section perpendicular to the main proximal-distal axis of the insertion section (i.e. the axis along the length of the insertion section), parallel to the inferior or superior surface, as the case may be.

By laterally we mean generally perpendicular to the proximal-distal axis of the insertion section.

In order to ensure sterility, and to obviate the need to repeatedly sterilise the entire laryngoscope, insertion sections of modern laryngoscopes are frequently removable and for example comprise a disposable protective cover for hardware such as cameras, image guides, light sources etc., and which is securable to the laryngoscope body, for example, to a hardware containing member extending from the body, or around the body, or a part thereof.

In order to minimize trauma to the patient and to provide the maximum room for further medical apparatus to be introduced into the oral cavity or airway, the size of the laryngoscope and in particular the laryngoscope insertion section is advantageously kept to a minimum, particularly the distal portion of the insertion section.

Additionally, since laryngoscopic procedures may require some forceful manipulation of the laryngoscope, it is additionally desirable that the insertion section and the medical instrument as a whole, be both light weight and mechanically robust.

Thus, whereas it is possible to produce robust insertion sections, strength may be at the expense of light weight and large dimensions, and whereas it has been possible to produce comparatively slimline insertion sections, this has been at the expense of durability or suitability for certain procedures and it is known for disposable laryngoscope insertion sections to be either prone to cracking during use, requiring replacement of the disposable portion, or worse resulting in injury or increased risk of infection, or sufficiently large as to be difficult to work with. Furthermore, if the insertion section bends too much under excessive force, the view of the larynx may be compromised.

SUMMARY OF THE INVENTION

According to a first aspect of the present invention there is provided a laryngoscope insertion section having a proximal portion, an intermediate portion, and a distal portion, a curved superior surface and a curved inferior surface, and a channel extending from the proximal end of the insertion section and through at least part of the intermediate portion, the channel having an inferior internal surface, wherein the curvature of the inferior internal surface is greater than the curvature of the inferior surface of the intermediate portion.

Preferably, the distance between the inferior and superior surfaces is at a maximum within the intermediate portion.

Thus, the thickness and therefore the strength of the laryngoscope insertion section is at a maximum in the intermediate portion. In use, when the insertion section has been secured to a laryngoscope and has been inserted into a patient's mouth (which process may typically be conducted without a great deal of mechanical force) the insertion section of the present invention is narrow where there is restricted room; in the proximal portion, which region of the patient's teeth, and the distal portion, which is in the region of the patient's larynx, and thicker in the intermediate portion, where there is more space; in the patient's oral cavity. Thus, when mechanical force is applied, damage to the patient's teeth may be kept to a minimum.

It is known that stress within a laryngoscope insertion section (from forces applied to the distal portion of the laryngoscope insertion section through manipulation of the patient's airway, and forces applied to the proximal portion through manipulation of the laryngoscope body by the medical practitioner) is typically concentrated in the intermediate portion, and cracking or even snapping of known laryngoscope insertion sections in the intermediate portion is a known potential risk. Furthermore, if the insertion section bends too much under excessive force, the view of the larynx may be compromised. Thus, the present invention advantageously provides maximum mechanical strength in the portion wherein, in use, the most stress is received and the most space is available.

The proximal portion may comprise an engaging formation for releasably securing the laryngoscope insertion section to a laryngoscope body. The laryngoscope body may include the laryngoscope handle. The insertion section may include the laryngoscope handle. The laryngoscope body may fit into the channel at least in part. The laryngoscope body may comprise a video camera.

Typically, the channel extends from the proximal end of the insertion section through the proximal portion and through at least part (or all) of the intermediate portion.

The channel may have a constant cross section along all or a substantial part of its length.

Video laryngoscopes, wherein the view of a patient's oral cavity is provided to an integral or remote screen, via an image capture device positioned in the laryngoscope insertion section, are now in widespread use. Video laryngoscopes are typically used provide an indirect view of the glottis or trachea although the invention can be employed for direct or indirect laryngoscopy or provide a device suitable for either direct or indirect laryngoscopy. It is known for a laryngoscope to comprise an elongate hardware containing member, which is typically rigid, extending from the body, and sized to be slideably received within the channel of a removable laryngoscope insertion section, the elongate members having generally the same curvature as the inferior surface of the insertion section, so as to minimize the dimensions of the insertion section.

It is known for laryngoscope insertion sections to curve (or lift) anteriorly close to their distal end to provide an improved anterior view of the patient's oral cavity. Such devices do not provide a good direct view. Certain medical procedures, or medical procedures under certain circumstances (for example emergency circumstances, in lighting conditions which make viewing a screen difficult, or when electrical power to a video laryngoscope is lost) require the medical practitioner to have a direct view.

The laryngoscope insertion section of the present invention is preferably provided with an inferior surface of sufficiently low curvature that direct viewing is possible, in use, but is provided with a channel having greater curvature to encompass the curvature of the hardware containing member of a video laryngoscope having correspondingly greater curvature.

Thus, the present invention enables a video laryngoscope adapted for use with demountable insertion sections and optimized to provide an indirect anterior view, to be connected to an insertion section permitting a direct view.

Typically, the curvature of the channel is substantially equal to the curvature of the superior surface. Thus, the dimensions of the insertion section may be kept to a minimum.

In some embodiments, the curvature of the inferior surfaces of the intermediate and distal portions, are exceeded by the curvature of the inferior surface in the region of the interface between the intermediate and distal portions. Thus, the distal portion (which is typically formed as a laryngoscope blade) extends at a more pronounced curve, or more anteriorly, from the intermediate portion, until straightening towards the distal end, such that there is a region of the inferior and superior surfaces at the region of the interface between the distal and intermediate portions with increased curvature (in comparison to adjacent regions), so as to provide an improved anterior view, in use with a video laryngoscope.

In some embodiments, the curvature of the inferior and/or superior surface of the intermediate and distal portions, are not exceeded by the curvature of the inferior and/or superior surface in the region of the interface between the intermediate and distal portions. Thus, there is provided a smooth transition between the intermediate and distal portions, such that stress is not focussed (for example as might be the case where the distal portion extends at an angle from the intermediate portion) in the region of increase curvature. Thus, such laryngoscope insertion sections might be most suitable for medical procedures requiring the application of substantial mechanical force.

The distal portion typically has a thickness which tapers along its length, being least at the tip.

In some embodiments, wherein the curvature of the inferior surface is defined by an inferior radius, and the curvature of the superior surface is defined by a superior radius, the superior radius is smaller than the inferior radius. The curvature of the inferior internal surface may be defined by an internal radius, wherein the internal radius is smaller than the inferior radius.

In some embodiments, an aperture extends through the intermediate portion between the inferior surface and the superior surface. The aperture may be elongate and may have a superior inner surface substantially parallel to the inferior surface.

An aperture so positioned reduces surface stress on the inferior surface. When a laryngoscope insertion section flexes, in use (from forces applied to the distal and or proximal portions), the inferior surface is placed in tension and the superior surface is placed in compression. The inferior surface also tends towards the superior surface and forces are thus generated generally perpendicular to the said surfaces. Provision of an aperture, and in particular an elongate aperture, allows the inferior surface to move in relation to the superior surface and thus relives stresses in the region of the inferior surface, which are generated generally perpendicular to the said surfaces, in use.

The laryngoscope insertion section may comprise a plurality of apertures extending through the intermediate portion (and, in some embodiments, the distal and or proximal portions) between the inferior surface and the superior surface.

The provision of one or more apertures allows the total amount of material of the laryngoscope insertion section to be minimized, thereby reducing the mass of the medical device so as to minimize patient trauma in use. Reduction of the mass of the insertion section also improves the balance of the laryngoscope, rendering the apparatus easier to use.

Furthermore, for a given mass and size of insertion section, the provision of an aperture in the intermediate portion increases the flex of the intermediate portion, in relation to the distal portion, when force is applied to the inferior surface, in use. This is particularly advantageous since deflection of the distal portion of a laryngoscope insertion section by several millimeters, as typically occurs during use of a laryngoscope, may impair the direct (or, where applicable, the indirect) view of the patient's trachea and epiglottis. This problem does not occur to the same extent if the intermediate portion flexes. Indeed, reduction of the curvature of the intermediate portion of the inferior surface (as provided by the or each aperture) when the intermediate portion flexes, in use, further improves the direct view. Thus, the direct view is improved by virtue of both the reduced flex of the distal portion and the increased flex of the intermediate portion of the inferior surface.

It is therefore advantageous to provide of one or more apertures in the intermediate portion.

Furthermore, laryngoscope insertion sections typically comprise a plastics material and may be manufactured by moulding or extruding a plastics material at an elevated temperature. Therefore, minimizing the amount of material, for example by providing one or more apertures or providing a channel having substantially the same curvature as the superior surface, or any other means of reducing the amount of material disclosed herein, reduces the heat capacity of the insertion section and accumulations of thermal energy during manufacture, such that stress introduced by the temperature changes during manufacture is less liable to be present within the material of the insertion section and the production of insertion sections having more consistent mechanical properties is thereby enabled. Additionally, use of a minimum of material enables materials costs to be minimised and also enables more rapid manufacture (e.g. by virtue of more rapid cooling of plastics material following injection moulding or extrusion at elevated temperatures) so as to reduce costs. Thus, disposable insertion sections may be cost effectively employed for a wider range of procedures.

The (or each) aperture may extend through the intermediate portion between the inferior surface and the channel.

In some embodiments, instead of an aperture there is provided a recess extending the majority of (and typically at least 80% or at least 90%) the way through the intermediate portion, between the inferior surface and the channel. Optional features of the recess correspond to those set out above in respect of the aperture. Although an aperture is generally preferred, some of the benefits of the aperture may be obtained using a said recess.

Optionally, a strengthening member may is provided in the channel. The strengthening member may extend from a laryngoscope body and may be integral to the laryngoscope insertion section. The laryngoscope insertion section may be removable from a laryngoscope body and the strengthening member may be slideably removable from the channel.

In some embodiments, a strengthening element is provided in the intermediate portion. The strengthening element may be integral to the insertion section. For example, plastics material may be formed around a strengthening element (for example a metallic strengthening element) during manufacture.

The strengthening element may further extend within the distal portion.

A plurality of discrete strengthening elements may be provided.

Alternatively, or in addition, the distal portion may comprise one or more strengthening elements, so as to further reduce the flexing of the distal portion in comparison to the intermediate portion, in use.

Preferably, at least part of the strengthening element is planar.

The strengthening element may be a printed circuit board. The printed circuit board may be oriented in the plane of the laryngoscope insertion section (and handle).

In embodiments wherein an aperture extends through the intermediate portion between the inferior surface and the superior surface, at least part of the strengthening element may extends between the inferior surface and the aperture.

Thus, the portion of the laryngoscope insertion section which is placed under the greatest amount of tension, when forces are applied in use, may be reinforced with a strengthening element, which is most preferably composed, or comprises, a material (for example a metal) which is strong in tension.

In embodiments wherein an aperture may extend through the intermediate portion, the aperture may extend through the strengthening element, between the inferior surface and the superior surface. Thus, a single strengthening element may provide strength to the portion of the laryngoscope insertion section which is placed under the greatest amount of tension, in use, and provide strength to one or more other parts of the implement.

Preferably, the strengthening element extends along the at least some of length of the insertion section, a first portion of the strengthening element is generally parallel to the interior surface and a second portion of the strengthening element is generally perpendicular to the inferior surface, and the first and second portions of the strengthening element meet along at least part of the length of the laryngoscope insertion section through which the strengthening element extends.

A third portion of the strengthening element may, in some embodiments be generally parallel to the superior surface, and the first and second portions, and the second and third portions, of the strengthening element meet along at least part of the length of the laryngoscope insertion section through which the strengthening element extends, the strengthening element thereby formed in the shape of a girder along at least part of the length of the laryngoscope insertion section.

The strengthening element may therefore have an L-shaped or girder shaped cross section along at least part of its length. The strengthening element may be U-shaped or I-shaped. Accordingly, additional strength may be provided by the strengthening element (or strength may be provided by the strengthening element using less material).

The laryngoscope insertion section may comprise a plurality of strengthening elements (which may be integral to the insertion section) positioned in regions through which, in use, the highest forces are transmitted and/or the greatest amount of flex would otherwise be caused.

For example, the insertion section may comprise one or more strengthening elements in the distal portion. Typically, the distal portion narrows towards the distal end of the insertion section (and is thus formed as a laryngoscope blade). Typically also, forces are applied to the patient's trachea and epiglottis through the distal portion. Therefore, the distal portion of known laryngoscope insertion sections are known to flex and/or require additional material and size to provide adequate stiffness. Provision of one or more strengthening elements enables a smaller distal portion to be used.

For example, the insertion section may additionally (or alternatively) comprise strengthening elements in the region between the intermediate and distal portions. Particularly where the distal portion is very stiff, stress builds up in this region.

For example, the insertion section may additionally (or alternatively) comprise one or more elongate strengthening elements between the aperture and the channel, extending generally parallel to the inferior surface along the length of the intermediate portion. The elongate strengthening element or elements may be wires (for example metal wires) or threads or filaments of a material which is strong in tension (such as a plastics or composite material).

The or each said strengthening element is typically a metal strengthening element (for example stainless steel) but may be composed of any suitable secondary material, such as a rigid plastics material or a composite material.

One or more of; a camera, a light source, a light guide, a strengthening member, an image capture device, a gas supply; may be provided in the channel. A lens may be provided at the distal end of the channel.

In some embodiments, the laryngoscope insertion section further comprises a plurality of endotracheal tube guiding members extending laterally therefrom, having tube guiding surfaces which are arranged to contact and thereby guide the inferior or superior surface of a retained endotracheal tube introduced thereto.

Typically, the inferior surface extends laterally beyond the superior surface along all or a substantial part of its length. For example, the width of the superior surface may be determined by the width of the channel and the inferior surface (which functions to manipulate the tongue, in use) extends beyond the width of the channel (and thus the superior surface) on one or both sides.

In a preferred embodiments, at least one buttress extends laterally away from the inferior surface and an outer edge of the inferior surface. The cross section of the insertion section through the buttress is thus generally triangular, and functions to transmit force and thereby support the inferior surface extending laterally beyond the superior surface, in use.

The superior surface may similarly extend laterally beyond the inferior surface along all or a substantial part of its length. For example, the inferior surface may extend beyond the superior surface on one side of the insertion section, and the superior surface may extend beyond the inferior surface on the other side of the insertion section. Accordingly, the superior surface may similarly be provided with at least one buttress extending laterally away from the superior surface and an outer edge of the superior surface.

The angle between a plane perpendicular to the inferior surface (or superior surface, as the case may be) along the length of the laryngoscope insertion section and the superior surface of the or each buttress (or the inferior surface of the or each buttress, as the case may be) is preferably between 90 and 125 degrees, more preferably between 92 and 125 degrees and most preferably between 92 and 115 degrees. In a preferred embodiment, the angle is approximately 115 degrees.

In some embodiments, a buttress is positioned at or near the distal end of the channel. Typically, the greatest stresses are borne in the region between the intermediate and distal portions, and typically the channel extends through the intermediate portion to this high-stress region. Thus, a buttress in this region provides support to the inferior surface and the insertion section generally, where it will be most beneficial. In particular, where a strengthening member is provided in the channel, provision of a buttress so positioned enables stress to be transferred most effectively to the strengthening member. Alternatively, or in addition, a strengthening member or a portion thereof may be positioned to receive stresses from a buttress so positioned.

In some embodiments, the cross section of the laryngoscope insertion section in the region of the inferior surface (and/or the superior surface), along some or all of the length of the laryngoscope insertion section, tapers towards an outer edge, thereby functioning as one or more elongate buttresses.

Accordingly, the invention extends in a second aspect to a laryngoscope insertion section having a proximal portion, an intermediate portion, and a distal portion, having a superior surface and an inferior surface that extends laterally beyond the superior surface along all or a substantial part of its length, wherein at least one buttress extends laterally away from the inferior surface and an outer edge of the inferior surface.

The angle between a plane perpendicular to the inferior surface (or superior surface, as the case may be) along the length of the laryngoscope insertion section and the superior surface of the or each buttress (or the inferior surface of the or each buttress, as the case may be) is preferably between 90 and 125 degrees, more preferably between 92 and 135 degrees and most preferably between 92 and 115 degrees. In a preferred embodiment, the angle is approximately 115 degrees.

A channel may extend from the proximal end and through at least part of the intermediate portion, and, in some embodiments, a buttress is positioned at or near the distal end of the channel.

The cross section of the laryngoscope insertion along some or all of the length of the laryngoscope insertion section, tapers towards an outer edge of the inferior surface (and/or the superior surface), thereby functioning as one or more elongate buttresses.

In some embodiments, a strengthening member (or a hardware containing member functioning or comprising a strengthening member) may be provided in the channel. The strengthening member may be slideably received in the channel, or the channel may be sized to slideably receive a strengthening member (or a hardware containing member functioning or comprising a strengthening member) when the insertion section is connected to a laryngoscope body, in use.

Buttressed regions of the laryngoscope insertion section which are subject to significant forces in use, enable less material to be used elsewhere, thus keeping total amount of material to a minimum (therefore improving weight distribution, costs and manufacturing consistency). This is more efficient and can reduce waste. Similarly, material reduction through the use of one or more apertures makes more material available for use in other structural elements, such as buttresses.

The laryngoscope insertion section may comprise a plurality of generally triangular prismatic formations extending parallel to the length of the insertion section. For example, one or more buttresses may have a generally triangular prismatic cross-section.

In embodiments comprising a strengthening member (or adapted for use with a slideably received strengthening member) the wall thickness of the channel may be significantly reduced in comparison to insertion sections lacking such buttresses or buttressed regions.

For example, known laryngoscope insertion sections comprising a channel typically comprise a constant thickness of material throughout, and are manufactured from sheet metal or extruded plastics. Consequently, excess material is present in some regions, and it may be that insufficient material (and strength) is present in other regions, the overall mechanical properties being a compromise. Whereas, the insertion section of the present invention may be provided with different thicknesses of material in different regions, varying for example from less than 1 mm thickness in the wall of the channel (the channel having a strengthening member, or adapted for use with a strengthening member) to 3-9 mm in a buttressed region.

In some embodiments, the thickness of wall of the channel may be approximately 0.6 mm, or 0.1 mm.

Accordingly, the invention extends to a laryngoscope insertion section having a proximal portion, an intermediate portion, and a distal portion, and a channel extending from the proximal end of the insertion section and through at least part of the intermediate portion, the channel defined by at least one wall (which may be straight or curved) between an inner surface of the channel and an outer surface of the insertion section, the laryngoscope insertion section having an inferior or superior surface that extends laterally beyond the outer surface of the laryngoscope insertion section along all or a substantial part of the length of the channel, and wherein at least one buttress extends laterally away from the inferior surface and an outer edge of the inferior surface, wherein the thickness of the or each wall along some or all of the length of the channel, is less than one third, preferably less than one fifth, and more preferably less than one tenth of the maximum depth of the or each buttress.

In some embodiments, the thickness of the or each wall along some or all of the length of the channel is less than 1.5 mm, preferably less than 1.3 mm, or less than 1 mm, and may be approximately 0.7 mm, or approximately 0.1 mm.

For example, the thickness of one or more walls of the channel may be 0.1-1 mm and the thickness of one or more buttresses or other structural elements of the insertion section may be 2-8 mm.

Further preferred and optional features of the insertion section of the second aspect correspond to preferred and optional features of the first aspect.

The laryngoscope insertion section according to the first or second aspects may be disposable, or adapted for limited or single use. The insertion section may for example comprise spoiling means.

In some embodiments of the first or second aspects, the curvature of the superior surface of the proximal portion is the same or substantially the same as the curvature of the superior surface of the intermediate portion. Typically, the curvature of the proximal portion of the superior surface is reduced, such that strength is provided between the insertion section and the laryngoscope body. Continuation of substantially the same curvature of the superior surface to the proximal portion advantageously narrows the depth of the insertion section in the region of the patient's teeth, in use. Provision of a channel enables a strengthening element to be provided in the channel, such that increased depth of the proximal portion is unnecessary.

In embodiments having a channel extending from the proximal end and through at least part of the intermediate portion, the channel may have a constant cross section throughout its length. In some embodiments, the cross section (area, or shape) of the channel varies along its length. For example, the cross section of the channel may reduce towards the distal end of the channel.

The channel typically has a generally square or rectangular cross section. In some embodiments, the channel has an alternative cross section (and may be adapted to receive a hardware-containing member having a corresponding cross section). For example, the channel may have a circular or oval cross section, or may have a triangular or polyhedral cross section. Alternative cross sections may advantageously provide room for additional channels or further apparatus, such as a tube guide or a light source, such that external dimensions of the insertion section, or the insertion section when an endotracheal tube is in the tube guide, may be minimized.

Alternative channel cross sections may enable a smoother external surface of the insertion section (as compared to square, rectangular, triangular or other polyhedral cross sections) so as to minimize patient trauma. This may be particularly advantageous for smaller sized of insertion sections, for example insertion sections sized for use with children.

Furthermore, alternative channel cross sections, such as triangular cross sections may provide additional structural rigidity, or may enable the insertion section to be used with a strengthening member (which may be a hardware containing member, or hardware containing member comprising one or more strengthening members) having cross sections which provide additional structural rigidity.

The hardware containing member, or strengthening member, as the case may be, may be provided with a keyed profile (for example an indentation or a protrusion along its length) and the insertion section may be provided with a channel having a cooperating keyed profile. Thus, the insertion section may only be slideably engaged with a compatible hardware containing member, or a strengthening member and/or may only be slideably engaged with a hardware containing member in the correct orientation.

Thus, the invention extends in a further aspect to a laryngoscope (or other type of intubation instrument) comprising a body and an elongate member extending from the body, in slideable engagement with a laryngoscope insertion section, the elongate member having a cross section provided with at least one keyed surface profile along at least part its length, and the channel having cross section provided with at least one cooperating keyed surface profile along at least part of the length of the channel.

The keyed surface profiles may be provided along the entire length of the elongate member and the channel. The keyed surface profiles may extend around part, or all, of the circumference of the cross sections (any may therefore be keyed cross sections, of the channel and elongate member). The elongate member may cooperatively and slideably engage with the channel along all or a part of the length of the channel (and of the elongate member), around a part or the entire circumference of the cross sections of the channel and elongate member.

The elongate member may comprise or consist of hardware such as an image capture means, light source and/or a strengthening member.

The insertion section is preferably releasably secured to the elongate member (so as to enable its removal for cleaning or disposal).

Keyed surface profiles provide improved fit and positioning of rigid or flexible elongate members, within the channel. For example, in embodiments wherein the elongate member is flexible, or straight, a keyed surface profile ensures that the insertion section and elongate member may only slideably engage in a single orientation (unlike some known intubation instruments having round, square or symmetrically cross sectioned elongate members and channels, which permit the insertion section to be incorrectly engaged with the elongate member).

Furthermore, keyed cross sections ensure that only insertion sections which are compatible with the elongate member and/or body may be slideably engaged therewith.

Thus, the elongate member may have a constant cross section along its length, or may have one or more different cross sections along its length, for example a keyed cross section along part of the length of the elongate member. In some embodiments, the elongate member tapers and has a cross section which generally reduces towards its distal end (and which may be provided with a keyed profile along some or all of its length).

The keyed profile may comprise an indentation or protrusion along at least part of the length of the elongate member, and a corresponding protrusion or indentation (respectively) on an inner surface of the channel.

The cross section of the elongate member (and the channel), along all or a part of its length, may be an asymmetric polyhedron (such as an asymmetric quadrahedron), or may be trapezoidal, the cross section may be an isosceles triangle, or may be a polyhedron having at least one curved edge, or may be provided with any suitable profile such that the elongate hardware containing member is slideably engageable in a single orientation in relation to the insertion section.

The keyed cross sections of the elongate member (particularly in embodiments wherein the elongate member is adapted to strengthen the insertion section) and/or the channel may be adapted to strengthen the insertion section and/or the elongate member.

Known intubation instruments having insertions sections slideably engaged with an elongate member may have square or round cross sections. A suitably oriented keyed cross section such as a triangular cross section, or a trapezoidal cross section, may more effectively resist forced applied to the insertion section in use.

The elongate member may be rigid, resilient or flexible.

The elongate member may comprise, or consist of, a strengthening member, to strengthen the insertion section of the intubation instrument. For example, the elongate member may be of generally tubular construction, one, or more, or all, sides of which are composed of a resilient or strengthening material, such as a metal (e.g. stainless steel or titanium). Alternatively, or in addition, a strengthening rod or tube may extend within the elongate member.

The elongate member may comprise, further comprise, or consist of, an image capture means and/or a light source. The image capture means may be a camera, typically located at the distal end of the elongate member, with one or more electrical conductors (which may be one or more wires, or which may be a metallic strengthening member) extending from the camera to the body. The camera may comprise a lens, or a lens may be provided at the distal end of the channel. The image capture means may be an optical fibre, or an optical fibre bundle, operable to convey an image to a camera located in the body or otherwise in communication with the image capture means.

In some embodiments, the intubation instrument comprises a light source, operable to provide illumination at or near the distal end of the insertion section, so as to illuminate a patient's body cavity, in use (e.g. to enable an image capture means to capture an image of a patient's body cavity in the absence of ambient light. The hardware containing member may comprise the light source. The light source may be provided in the channel (for example the light source may be slideably introduced into the channel adjacent to the elongate member, or through the elongate member, when required during a medical procedure).

In some embodiments, the light source is integral to the insertion section. The insertion section may comprise a further channel, extending through at least part of the insertion section, the further channel having the light source therein. The light source may be slideably engageable with the further channel (for example, an optical fibre bundle functioning as a light source may be slideably introduced to the further channel as required). Typically, the further channel runs substantially parallel to the channel.

Typically, the light source is a light guide (for example an optical fibre or optical fibre bundle) operable to conduct light from a light source external to the elongate member.

Typically, know intubation instruments are provided with square, round or rectangular elongate members, for slideable engagement with an insertion section. Thus, the minimum external dimensions of the insertion section must be sufficient to accommodate both the elongate member and provide suitable functionality to the insertion section.

For example, a typical laryngoscope insertion section is typically provided with a spatulate shape to at least a distal portion thereof. Thus a laryngoscope insertion section adapted to slideably engage with an elongate member having a square or round cross section must further comprise a suitably sized channel extending along at least part of its length.

In relation to certain applications, for example for pediatric use, the external dimensions of an insertion section of an intubation instrument is advantageously minimized, and thus the size and function of such instruments may be compromised in order to accommodate hardware such as an image capture means.

Accordingly, in a preferred embodiment, the cross section of the elongate member and the channel conform generally to the cross section of the insertion section, along at least a part of the length of the insertion section. In embodiments comprising a further channel, the channel and the further channel are together disposed so as to conform generally to the cross section of the insertion section, along at least a part of the length of the insertion section.

For example, the cross sections may be L-shaped, such that a portion of the channel is aligned generally parallel to the inferior surface of the insertion section. In some embodiments, the insertion section is tapered towards one or more outer edges (as set out in relation to the alternative embodiments of the present invention) and the cross sections of the channel and the elongate member are provided with corresponding tapered profiles. In embodiments wherein the elongate member consists of or comprises a strengthening member, the requirement for the insertion section to have mechanical strength is reduced. Thus, the insertion section need only comprise a minimum of material necessary to cover the elongate member (along the length of the channel) and may therefore have minimum dimensions if the elongate member is provided with a suitable cross section.

The elongate member is preferably provided with a contiguous external surface. A contiguous external surface comprises no joints or seams which might become contaminated with dirt or infectious bodies.

The external surface of the elongate member may be a plastics material or may be a metal. In embodiments wherein the elongate member has a constant cross section along its length, the external surface (which may also function as a strengthening member) may be extruded, and thus be contiguous. The external surface may be an extruded tubular member (metallic or plastics).

In some embodiments, the elongate member is moulded and may be a moulded plastics material, and may be moulded over one or more pieces of hardware (such as an image capture means, a light source and/or one or more strengthening members), and thus comprise a contiguous outer surface.

Conventional laryngoscope insertion sections have an inferior surface which curved along the length of the insertion section and laterally generally flat. A generally laterally flat inferior surface, particularly of the intermediate portion, provides the best direct view of the patient's trachea and epiglottis, in use. However, when force is applied and the insertion section flexed in use, the outer edge of the inferior surface is pulled towards the inferior surface, and the inferior surface becomes laterally bowed towards the superior surface, compromising the direct view when force is applied.

Preferably therefore, the inferior surface is angled from the outer edge of the inferior surface towards the outer edge of the inferior surface. The inferior surface is preferably laterally convex.

Thus, when the insertion section flexes in use, and the outer edge of the inferior surface is deflected towards the superior surface, the inferior surface is drawn generally parallel to the superior surface, and, in embodiments having a laterally convex inferior surface, the curvature of the inferior surface is reduced. The insertion section is thereby optimised for direct viewing when flexed, in use. The optimal shape is typically present under normal operating forces.

Preferably, for example in embodiments having an aperture in the intermediate portion, the deflection of the outer edge of the inferior surface of the intermediate portion is greater than the deflection of the outer edge of the inferior surface of the distal portion.

The invention therefore extends in a third aspect to a laryngoscope insertion section having a curved superior surface and a curved inferior surface having an outer edge, wherein the inferior surface has concave lateral curvature and slopes from the outer edge of the inferior surface towards the superior surface when no force is applied to the inferior surface.

In use, when force is applied to the inferior surface, causing the insertion section to flex, the inferior surface is deflected towards the superior surface and the lateral curvature of the inferior surface is reduced.

Further preferred and optional features correspond to preferred and optional features of the first, second and sixth through ninth aspects.

The invention also extends in a fourth aspect to a laryngoscope insertion section having a curved superior surface and a curved inferior surface, and a channel extending through at least part of the length of the laryngoscope insertion section the channel having an inferior internal surface, wherein, at least one location the distance between the inferior internal surface of the channel and the inferior surface, directly inferiorly of the channel, is more than 2 mm.

Further preferred and optional features correspond to those discussed in relation to the first, second and third, and seventh through ninth aspects.

According to a fifth aspect of the invention, there is provided a laryngoscope comprising a body portion and a laryngoscope insertion section according to the first, second, third or fourth aspects. The insertion section may be releasably secured to the body portion.

One or more of; a camera, a light source, a light guide, a strengthening member, an image capture device, a gas supply; may be provided in the channel.

In some embodiments, a hardware-containing member extends from the laryngoscope body, and is slideably received within the channel. The hardware-containing member may function as a strengthening member and may comprise one or more, or all, of; a camera, a light source, a light guide, a strengthening member, an image capture device, a gas supply.

According to a sixth aspect of the invention, there is provided a kit comprising a laryngoscope body and a laryngoscope insertion section, having a proximal portion for releasable connection to the laryngoscope body, an intermediate portion, and a distal portion, having a curved superior surface and a curved inferior surface, and a channel extending from the proximal end of the insertion section and through at least part of the intermediate portion, the channel having an inferior internal surface, wherein the curvature of the inferior internal surface is greater than the curvature of the inferior surface, and the distance between the inferior and superior surfaces is at a maximum within the intermediate portion.

The laryngoscope body may comprise a plug demountable retainable within a channel of the laryngoscope insertion section.

The kit may comprise a plurality of laryngoscope insertion sections, of the first, second, third and/or fourth aspects. The kit may comprise laryngoscope insertion sections of different sizes.

Further preferred and optional features of the fifth and sixth aspects correspond to preferred and optional features of the first through fourth and seventh through ninth aspects.

The invention extends in a seventh aspect to a laryngoscope insertion section having a curved superior surface and a curved inferior surface, wherein, in an intermediate portion of the insertion section, the superior surface and the inferior surface have substantially constant radius curves, wherein the radius of curvature of the superior surface is less than the radius of curvature of the inferior surface.

Thus, the insertion section is thinner where it curves around a patient's palette than where it extends past a patient's teeth in use.

It may be that the superior surface has the same radius of curvature in a proximal portion of the insertion section, such that the superior surface of the proximal and intermediate portions of the insertion section describe an arc of a circle. The superior surface may curve with a smaller radius of curvature in a distal portion of the insertion section. Typically, the curvature of the inferior surface of the insertion section is different in a proximal portion of the insertion section from the curvature in the intermediate portion. It may be that, in a proximal portion of the insertion section, the superior surface and the inferior surface describe arcs of concentric circles.

It may be that, in the intermediate portion, the radius of curvature of the inferior surface is between 40 mm and 220 mm, preferably 60 to 180 mm and more preferably between 90 and 150 mm.

It may be that, in the intermediate portion, the radius of curvature of the superior surface is between 40 mm and 125 mm, and preferably between 70 mm and 95 mm.

The laryngoscope insertion section is either coupled to a laryngoscope body having a centre line or is configured for coupling to a laryngoscope body having a centre line. It may be that, in the intermediate portion, the distance between the said centre line and the centre of curvature of the inferior surface is less than 60 mm. Preferably, the distance between the said centre line and centre of curvature of the inferior surface is in the range 30 mm to 60 mm and the centre of curvature is on the side of the centre line towards the insertion section.

It may be that, in the intermediate portion, the distance between the said centre line and the centre of curvature of the superior surface is in the range 20 mm to 100 mm (more preferably 45 mm to 75 mm) and the centre of curvature is on the side of the centre line towards the insertion section.

Preferably, the centre of curvature of the inferior surface is closer to the said centre line than the centre of curvature of the superior surface.

Preferably, the distance between the insertion section and the centre of curvature of the inferior surface is greater than the distance between the insertion section and the centre of curvature of the superior surface.

Preferably, the insertion section is configured so that a user may obtain a direct or indirect view of the trachea during endotracheal intubation.

According to an eighth aspect of the invention there is provided a laryngoscope insertion section having a curved superior surface and a curved inferior surface wherein, in a proximal portion of the insertion section, the superior surface and the inferior surface substantially describe arcs of concentric circles.

That is to say, in the proximal portion, each of the superior surface and the inferior surface describe segments of circles having coincident centres. Thus, the proximal portion can be narrower than would be the case in, for example, a traditional Macintosh blade where the superior surface generally extends perpendicular to the length of the laryngoscope handle.

In a ninth aspect of the invention there is provided a laryngoscope insertion section having a curved superior surface and a curved inferior surface, wherein, in an intermediate portion of the insertion section, the superior surface and the inferior surface have substantially constant radius curves, wherein the centre of curvature of the superior surface and the centre of curvature of the inferior surface are at least 15 mm apart.

Preferably, in the intermediate portion, the distance between the centre of curvature of the inferior surface and the centre of curvature of the superior surface is less than 150 mm. Preferably, in the intermediate portion, the distance between the centre of curvature of the inferior surface and the centre of curvature of the superior surface is in the range 25 to 75 mm.

Optional features discussed in relation to any one of the first through ninth aspects of the invention are optional features of the seventh, eighth and ninth aspects of the invention.

According to a tenth aspect of the invention, there is provided a laryngoscope comprising a body portion and a laryngoscope insertion section according to the seventh, eighth or ninth aspects. The insertion section may be releasably secured to the body portion.

DESCRIPTION OF THE DRAWINGS

An example embodiment of the present invention will now be illustrated with reference to the following Figures in which:

FIG. 4 is a schematic side view of the laryngoscope insertion section.

FIG. 5a is a cross section of the insertion section of FIG. 4, through a;

FIG. 5b is a cross section of the insertion section of FIG. 4, through b;

FIG. 5c is a cross section of the insertion section of FIG. 4, through c;

FIG. 5d is a cross section of the insertion section of FIG. 4, through d;

FIG. 5e is a cross section of the insertion section of FIG. 4, through e;

FIG. 6 is a schematic side view of an alternative embodiment of a laryngoscope insertion section;

FIG. 8 shows an expanded cross sectional view of the laryngoscope insertion section of FIG. 6 through a;

DETAILED DESCRIPTION OF AN EXAMPLE EMBODIMENT

Figure 1:
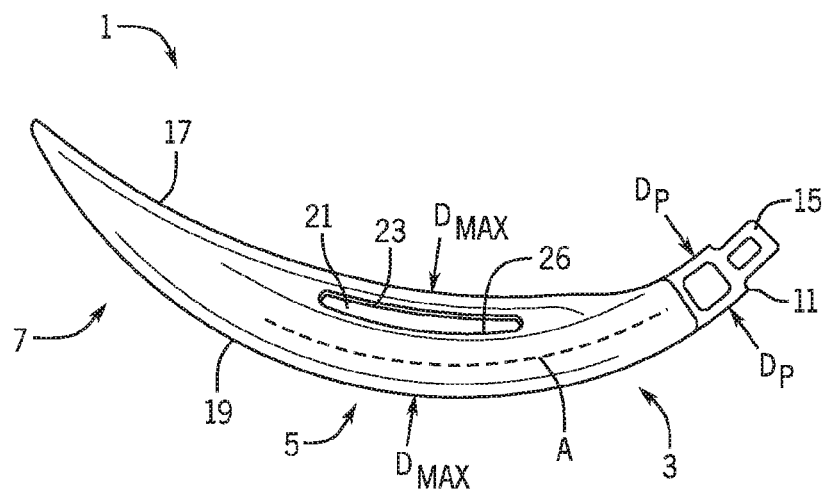
FIG. 1 is a side view of a laryngoscope insertion section.
Figure 2:
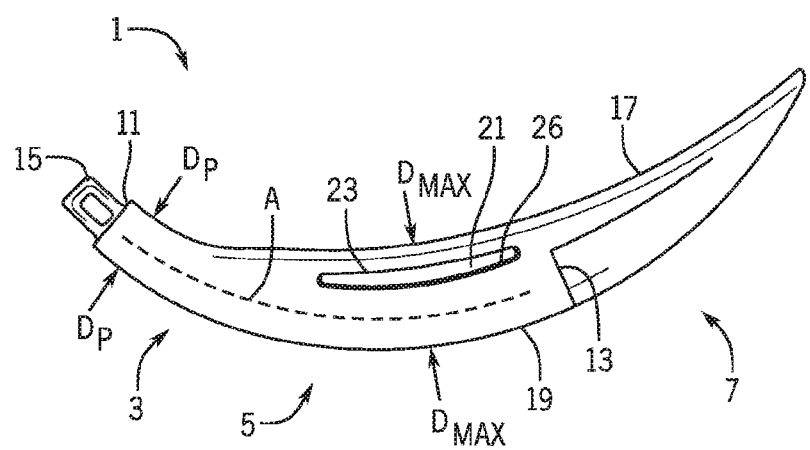
FIG. 2 is a side view of the laryngoscope insertion section of FIG. 1 from the opposite side.

FIG. 1 shows a side view of a laryngoscope insertion section 1 of the present invention, comprising a proximal portion 3, and intermediate portion 5 and a distal portion 7. A channel 9 (having a constant cross section throughout its length), the central axis A of which is shown in FIGS. 1 and 2, extends from the proximal end 11 through the proximal and intermediate portions of the insertion section. The distal end of the channel is provided with a lens 13, and the channel is sized to slideably receive a rigid laryngoscope camera stick (e.g., camera stick 28 illustrated in FIG. 12). Adjacent to the proximal end of the insertion section is provided a resilient tab 15 for removably securing the insertion section to a laryngoscope body.

The insertion section has a curved inferior surface 17, extending along a substantial part of the length of the insertion section, for engagement with a patient's tongue and epiglottis, in use, and a curved superior surface 19.

The curvature of the channel (and the inferior interior surface thereof, by virtue of the constant cross section of the channel throughout its length) is the same as the curvature of the superior surface.

The curvature of the channel and superior surface is greater than the curvature of the inferior surface.

Consequently, the depth of the insertion section reaches a maximum depth $D_{MAX}$ in the intermediate portion. Furthermore, as the curvature of the superior surface of the inferior portion extends to the proximal portion, the width $D_P$ of the proximal portion very small in comparison to many conventional laryngoscope insertion sections (such as Macintosh blades).

In alternative embodiments the curvature of the channel may differ from the curvature of the superior surface along some or all of its length, but is generally of substantially similar curvature along the portions of the insertion section through which the channel extends. In some embodiments, the cross section of the channel varies along its length and for example the cross section of the channel may decrease in size towards its distal end.

In the embodiment shown, the curvature of the superior and inferior surfaces are each defined by a single radius along their entire length. In alternative embodiments, the curvature of one or both surface may vary. For example, the curvature of the inferior surface may reduce at the distal portion, or the curvature of the said surfaces between the intermediate and distal portions may be greater than to either side, such that the distal portion extends at an angle from the intermediate portion.

An elongate aperture 21 extends through the intermediate portion between the channel and the inferior surface. A superior inner surface 26 and the inferior inner surface 23 of the aperture extend parallel to the inferior surface.

In use, the insertion section is slideably mounted over the camera stick (having a camera at its distal) of a video laryngoscope and secured to the body of the laryngoscope. Typically the camera stick also comprises a light source. During a medical procedure, the inferior surface is applied to manipulate the tongue of the patient, so as to provide an indirect view of the patients trachea and epiglottis, via the lens. The distal portion of the insertion section is used to manipulate the tissues of the glottis. The proximal region extends from the patient's mouth.

The insertion section is typically be gently and carefully introduced to the oral cavity, but thereafter it may be necessary to apply force (and in some cases substantial force). The proximal region extends from the patient's mouth and teeth and is thus advantageously of small dimensions so as to reduce the possibility of causing trauma to the patient's mouth and teeth when the laryngoscope is being forcibly manipulated, by virtue of the curvature of the superior surface of the proximal portion.

The curvature of the inferior surface, in comparison to the curvature of the channel and superior surface ensures that the insertion section is deepest and strongest in the intermediate portion, where the greatest stresses are received, and where there is largest amount of room (i.e. within the patient's oral cavity) during medical procedures.

In addition, the aperture reduces the stresses when the insertion section is caused to flex due to pressure on the distal portion of the inferior surface which are caused by the tendency of the inferior surface towards the superior surface.

The curvature of the inferior portion also permits a direct view, in use of the laryngoscope, whereas the curvature of the channel is compatible with camera sticks of video laryngoscopes which are optimised to provide an indirect anterior view. Interchangeability of insertion sections enables a single laryngoscope to be used in a variety of situations. For example, an insertion section of the present invention may be used in the event of electrical failure of the laryngoscope, such that procedures commenced with indirect anterior viewing may be completed with direct viewing, using a single laryngoscope body and camera stick.

Figure 3:
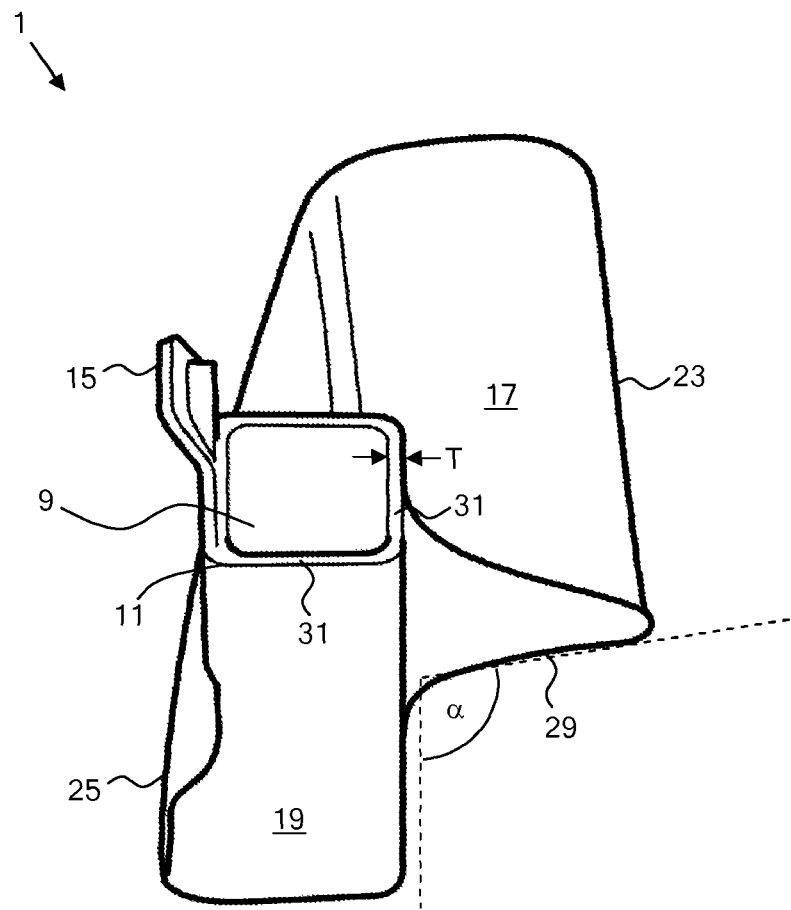
FIG. 3 is view of the laryngoscope insertion section of FIG. 1 from the proximal end.
Figure 7:
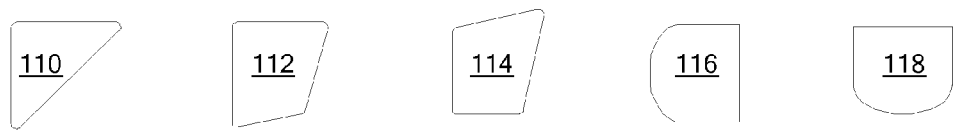
FIG. 7 shows a number or alternative channel cross sections.

As can best be seen in FIG. 3, the outer edge 23 of the inferior surface extends laterally beyond the superior surface along its length, and the outer edge 25 of the superior surface extends laterally beyond the inferior surface.

FIG. 4 shows a schematic side view of the insertion section 1, and the cross sections through a, b, c, d and e are shown, respectively, in FIGS. 5a-5e. The cross section tapers towards outer edges 23 and 25 along the length of the superior and inferior surfaces, so as to be formed generally as a buttress, providing mechanical strength to the insertion section (by virtue of the generally triangular shape) with a minimal material, in particular providing support to the inferior surface, which extends laterally to the greatest extent.

Typically the camera stick of a video laryngoscope also functions as a strengthening member (thus enabling the proximal portion to remain narrow). Thus, force transferred through the buttressed region 27 from the inferior surface in the region of the end of the channel, is transferred to the strengthening member. It is at this point that the greatest torque about the end of the strengthening member, from forces applied to the distal portion of the inferior surface, will be generated in use. Buttressed regions extending from the inferior and superior surfaces enable very thin channel walls, and the thickness T of the channel walls 31 (which may be most clearly seen in FIGS. 3 and 4) is less than 1 mm and (in some regions) as low as 0.6 mm.

Referring again to FIG. 3, the angle $\alpha$ between the superior surface of the buttressed region 29 and the plane perpendicular to the inferior surface along the length of the insertion section is optimally approximately 115 degrees. In alternative embodiments, the angle is greater or smaller along some or all of the length of the buttressed region or regions. For example, in some embodiments, the angle is smaller, so as to provide a tube guide and a pathway for an endotracheal tube introduced thereto.

FIG. 6 shows a further embodiment of a laryngoscope insertion section 100 of the invention. All of the external features of the insertion section 100 are identical to insertion section 1, discussed above.

Insertion section 100 comprises a metallic strengthening element 102, embedded in the intermediate and distal portions. The strengthening element is generally planar and extends generally perpendicular to the inferior and superior surfaces and is thus able to resist bending forces applied to the inferior surface in use. In addition, the aperture 121 extends through the strengthening element, such that a tensioning portion 140 of the strengthening element extends through the intermediate portion of the insertion section between the aperture and the inferior surface. The tensioning portion of the metal strengthening element is advantageously strong in tension and thus able to improve resistance of the inferior surface to the tensile forces which are applied in use.

In some embodiments, the strengthening element additionally extends parallel to the inferior surface in the intermediate and distal portions, the two planar regions of the strengthening element meeting at approximately 90 degrees along the length of the said portions of the insertion section. Optionally, the strengthening element may comprise a third planar portion extending parallel to the superior surface of the intermediate and/or proximal portions, such that the strengthening element is formed as a U-shaped girder around the channel in at least the intermediate portion, so as to provide additional strength to the insertion section.

The cross section of the channel of the insertion sections depicted in FIGS. 1-6 is generally square and constant along the length of the channel. In alternative embodiments, the channel may be provided with a cross section which varies along the length of the channel, or may be provided with cross sections of different shapes, for example the cross sections 110, 112, 114, 116 and 118.

A triangular cross section 110 may provide room for a tube guide adjacent to the channel, such that an endotracheal tube (or the tube guide elements) do not extend from the channel laterally as far as if the channel where of a square cross section. Polyhedral cross sections such as 112 or 114 provide room for additional tubes, light sources, strengthening members, or other apparatus to be inserted into the channel, in addition to a cameral stick having a generally square cross section. Cross sections with one or more rounded surfaces, such as 116 or 118, enable a smoother outer surface of the insertion section, which helps to reduce patient trauma where there is particularly limited space, in use (for example in medical procedures involving children).

Conventional insertion sections have an inferior surface which curved along the length of the insertion section but generally flat, laterally. A generally laterally flat inferior surface provides the best direct view of the patient's trachea and epiglottis, in use. However, when force is applied and the insertion section flexed in use, the inferior surface becomes laterally bowed towards the superior surface, compromising the direct view when force is applied.

Figure 8:
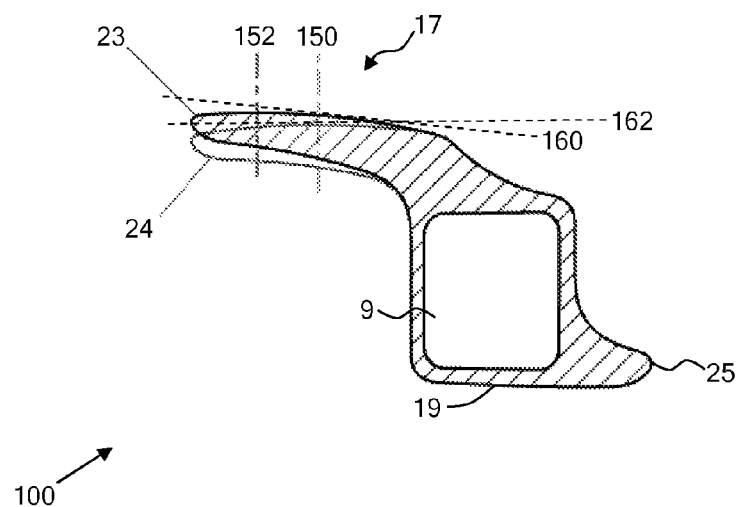

FIG. 8 shows a further view of insertion section 100 through line a (of FIG. 6). The inferior surface is provided with a slight lateral curvature, in contrast to conventional insertion sections. The apex of the lateral curve 150 (at the lateral midpoint of the inferior surface) has a tangent 160 which angled towards the outer edge 25 of the superior surface.

When force is applied causing the insertion section to flex, in use, as with conventional insertion sections, the outer edge 23 of the inferior surface tends towards the superior surface, as shown by position 24. The apex of the lateral curvature extends outwards to position 152, such that the inferior surface extends generally parallel to the superior surface, as shown by tangent 162 of the midpoint of the interior surface, and such that the lateral curvature of the inferior surface is reduced, when the insertion section is flexed Accordingly, the inferior surface adopts the optimal position to provide a direct view of the patient's trachea and epiglottis, when force is applied in use.

Since the ability for a medical practitioner to obtain a direct view is principally determined by the curvature of the intermediate portion, the additional flex of the inferior surface in the region of the aperture is particularly advantageous.

Figure 9:
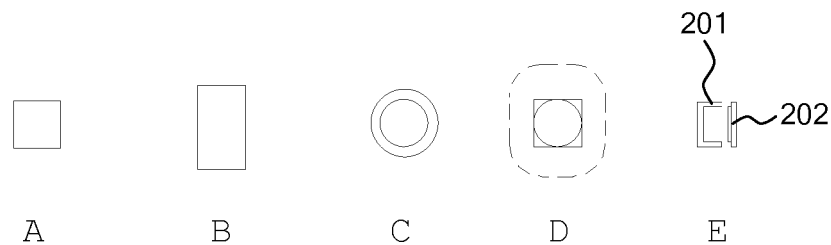
FIG. 9 shows various cross sectional profiles of known laryngoscope inserts.

FIG. 9 shows cross sectional profiles A-E of known laryngoscope inserts (typically elongate hardware containing members comprising a camera or optical fibre bundle functioning as an image capture means, and/or a light source), adapted to slideably engage with insertion sections having a channel extending partially therethrough, the channel having a corresponding cross section.

Previously known inserts may have a cross sections with a height:width ratio of approximately 1:1 (cross section A), or may be provided with a rectangular cross section (cross section B). Typically, the long sides of inserts with cross section of type B extend generally perpendicular to the inferior surface of a laryngoscope blade secured thereto. Inserts with cross sections of types A and B are typically rigid, may be of constant cross section or may taper from the body of the laryngoscope toward the distal end of the insert, and may function to strengthen the insertion section. Inserts are known which have a cross section of type B at the proximal end and which taper to, or towards, a cross section of type A at the distal end (i.e. the height:width ratio reduces towards the distal end).

Cross section C is characteristic of known flexible inserts (i.e. flexible elongate members which typically consist of an optical fibre bundle within a flexible plastics casing, the optical fibres functioning as image capture means and/or a light source, or flexible elongate members comprising wiring in communication with a camera, such as a CCD, at the distal end thereof).

Cross section D illustrates a known type of insert known as a "video baton" that begins with a larger cross sectional area at its proximal end, then tapers to a generally circular cable-like shape along its length (and through the insertion section of the laryngoscope), and having a generally square cross section at its distal end (where camera and illumination elements are located) with a height:width ratio of approximately 1:1.

Construction of such known laryngoscope inserts is typically complex. Exploded cross section E illustrates the typical construction of rigid inserts (for example A or B).

Rigid inserts are conventionally constructed in two parts 201 and 202 and joined (by gluing or welding) along their length during production processes.

Production costs are increased in order to ensure that a seal is reliably made. In addition, the seam is the mechanical weak point of the of insert and may therefore be susceptible to splitting open through wear and tear, or on impact (e.g. if dropped). Furthermore, even a comparatively strong, seam or joint provides a dirt trap.

Known inserts may also be insertable into insertion sections in a number of orientations. For example a round cross sectioned insert may be slideably inserted in any orientation in a channel of an insertion section, and therefore additional torsional strain may be applied by a user twisting the insertion section about the insert to the correct orientation in order to secure the insertion section to the body. Similarly, a round, square or rectangular straight insert may be slideably inserted into the channel of an insertion section in a number of orientations, and incorrect engagement may prolong installation time and be undesirable in emergency medical situations. In addition, it may be possible to install incompatible insertion sections over known inserts.

Figure 10:
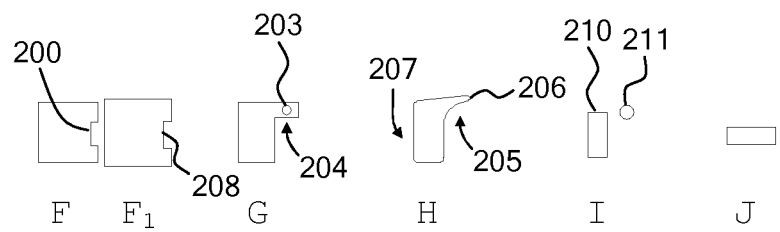
FIG. 10 shows various cross sections of intubation instrument inserts of the present invention.

FIG. 10 shows a number of cross sections F-J of intubation instrument inserts of the present invention. The cross sections F-J correspond to the cross sectional shapes of the channel of a suitable insertion section, or, in some embodiments cooperatively engage around a part of the circumference of the cross section and/or along a part of the length of the channel.

Cross section F comprises a keyed profile 200 that will allow improved fit and positioning for either rigid, partially rigid or flexible inserts which are slideably inserted into a channel with a cross section of type $F_1$ (which is provided with a corresponding keyed profile 208). Inserts having a keyed cross section such as F are also compatible only with insertion sections provided with channels having a corresponding keyed cross section, and vice versa.

Cross section G illustrates an alternative, generally L-shaped keyed cross section which conforms more closely to the cross section of an insertion section than known round or rectilinear cross sectioned inserts.

Further optical (or other) sensors or illumination devices 203 may be provided within the shelf area 204 (which aligns generally parallel to the inferior surface of an insertion section slideably engaged therewith) so that the space is used efficiently, thus facilitating a greater degree of miniaturisation than has previously been possible.

Cross section H is similar to cross section G, and conforms very closely to the cross section of the proximal and distal portions of an insertion section provided with a tapered buttress shape extending from the outer edge of the inferior surface. Accordingly, the shelf portion 205 of cross section H tapers towards outer edge 206. A rigid insert provided with cross section H along a part (and preferably all) of its length thus provides further structural support to the insertion section (e.g. a laryngoscope blade) that surrounds it, in operable use.

In one embodiment, the distal end of shelf portion 205 extends beyond the distal end of the open portion 207, so as to extend into the distal portion of a laryngoscope blade or other type of insertion section (provided with a suitable cavity extending from the channel) so as to provide structural support thereto.

Cross section I shows the cross section 210 of a narrow first insert, for insertion into a small channel in an insertion section. A second insert having cross section 211 may also be provided, to be optionally inserted into a corresponding further channel in an insertion section, the channel and further channel disposed so as to conform to the cross section of an insertion section, as shown in cross section I. The further channel may be adapted to receive a further probe, such as a light source, and the arrangement as a whole enables an intubation instrument having an insertion section of smaller dimensions than has previously been possible, operable to provide an improved line of sight to a user seeking a direct view of a patient's vocal cords etc. The first inset having cross section 210 may have a height:width ratio of 2.5:1 or more. In preferred embodiments, the width is less than 1 mm and the height is not less than 2.5 mm.

Cross section J is suited to low profile insertion sections, for example for patients with narrow mouth openings where access between teeth for example is less than 10 mm. The insert is typically oriented with the longer side generally parallel to the inferior surface of the insertion section, in use. The insert has a minimum height:width ratio of at least 1:1.5. In preferred embodiments, the insert has a height less than 2 mm and a width of not less than 3 mm.

Figure 11:
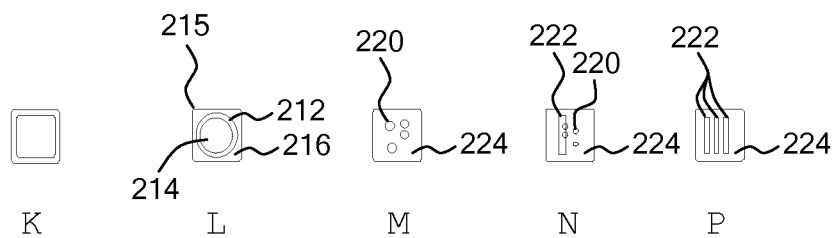
FIG. 11 shows various further cross sections of intubation instrument inserts of the present invention.

FIG. 11 shows a number of alternative intubation instrument insert cross sections K-P, of inserts having a constant cross section along their length. Such inserts, or their outer casings, are suitable to be extruded, electroformed, blow-moulded or cast, by any suitable method to create a contiguous outer surface. The outer surface may thus be rendered impermeable to water, and does not comprise surface features such as seams or joints which might become contaminated. Inserts so manufactured are therefore provided with improved structural integrity (by virtue of a lack of joints or seams) and are easier to clean and more hygienic.

Cross section K is a square cross section of an extruded insert casing.

Cross section L further comprises an inner core 212 such as metallic tube (that could be circular or of any other cross section) which provides still further strength, and having an bore 214 through which electronic or other hardware can pass. The outer material 215 may be a metal, or (since strength is provided by the inner core) the outer may be a plastics material that is cast or moulded onto the tube (and so occupies the entire of volume 216) to create a contiguous outer surface. In another embodiment, the inner core is flexible and is inserted into a resilient or rigid outer, or alternatively a resilient or rigid outer material may be cast or moulded over the inner core, so as to provide structural integrity.

Cross section M is of an insert comprising a number of individual cables 220 (which may be conductors and/or optical fibres and/or capillaries) moulded or cast into the insert, during manufacture.

Cross section N shows the cross section of an insert further comprising an encapsulated strengthening member 222. In some embodiments, the strengthening member functions, during manufacture, as a mounting for sub-assembled cables prior to the casting or moulding of the outer material 224. The strengthening member may be fully or partly embedded within the outer material. It may also function as a electrical ground, or carry current or other electrical signals from electrical apparatus (such as a camera) at the distal end of the insert, or at the distal end of the channel.

Cross section P shows a cross section of an insert having a number of strengthening members 222. In the embodiment shown, the plurality of strengthening members are generally planar and parallel to one another, and extend generally perpendicular to the inferior surface of the insertion section so as to resist flexing of the insertion section in use. Optionally, the insert may comprise individual optical or electric cables (not shown), which may be supported, as a sub assembly, by one or more of the strengthening elements, during manufacture.

Figure 12:
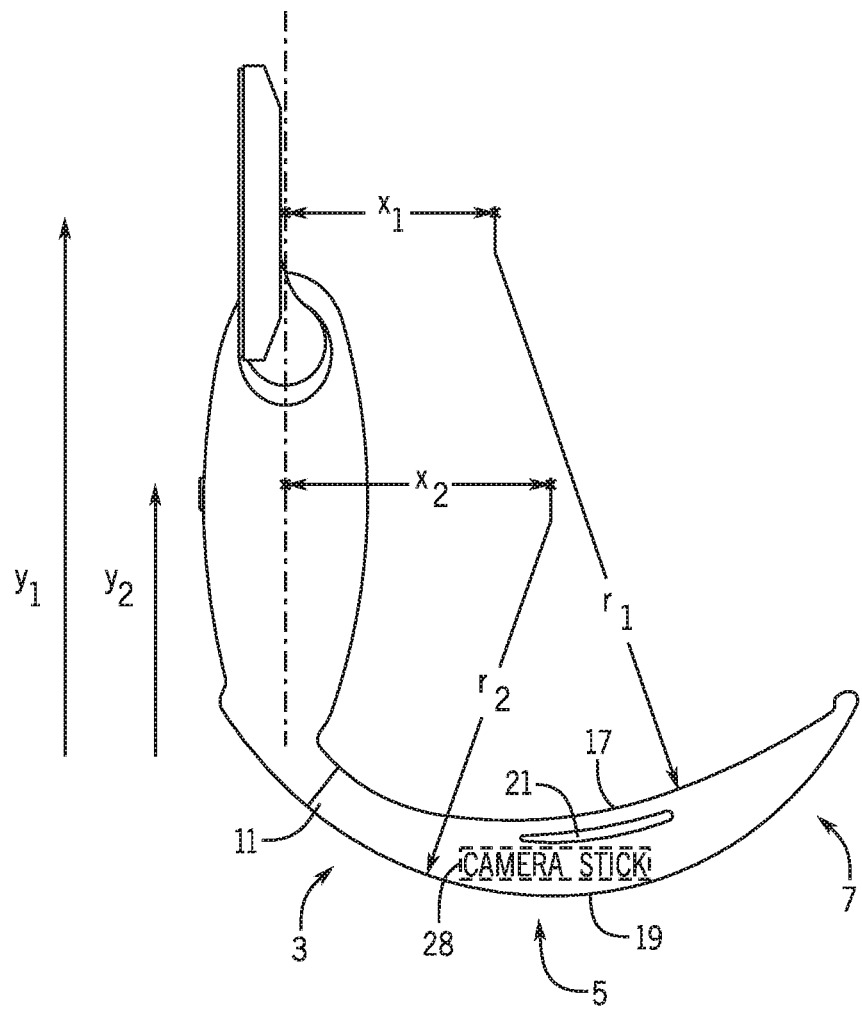
Figure 13:
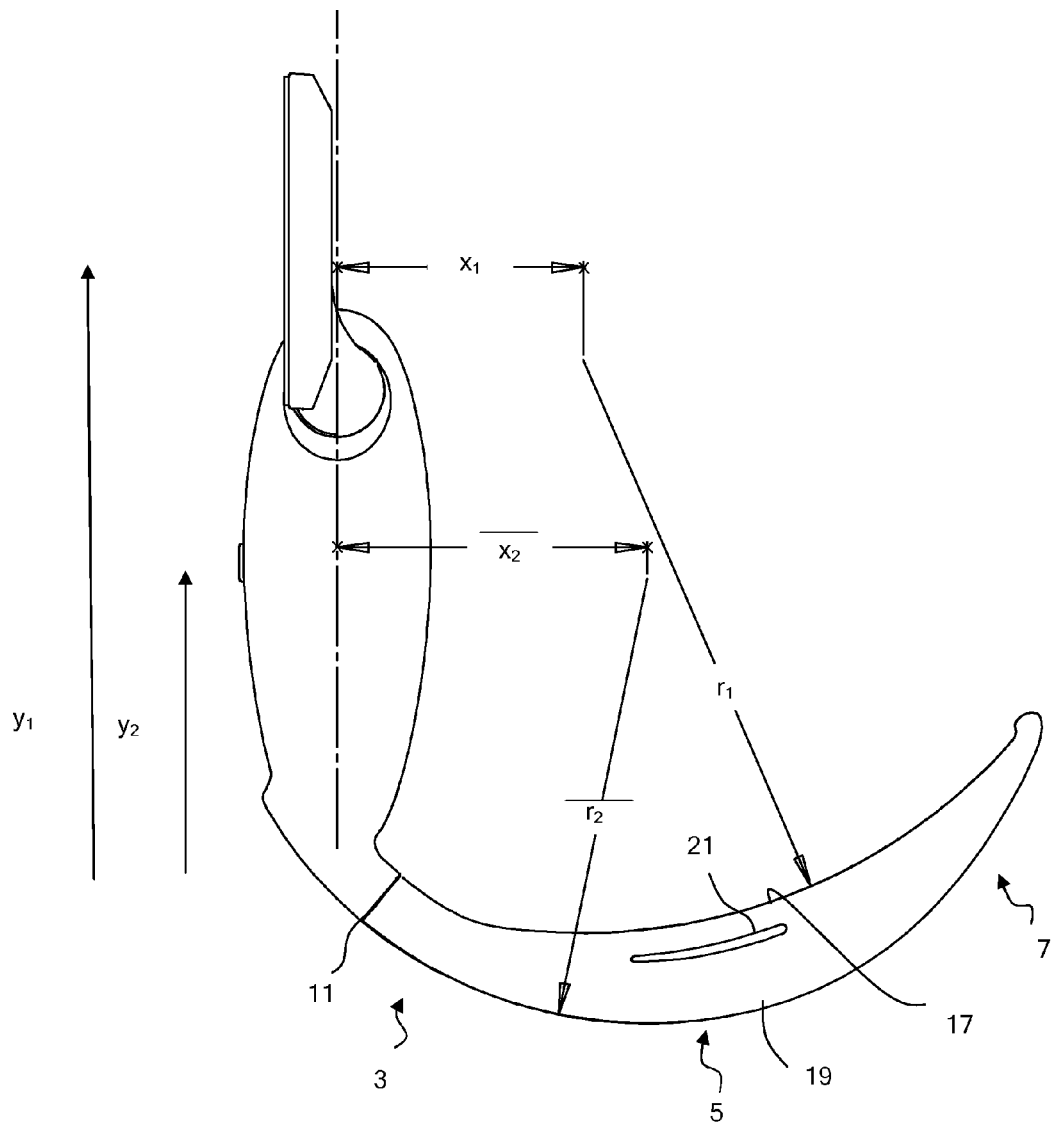

There are a number of other advantages to the shape of the inferior and superior surfaces of the laryngoscope insertion section. FIGS. 12 and 13 are cross-sections through a laryngoscope with insertion section. The intermediate portion of the insertion section has an inferior surface 17 and superior surface 19 which are substantially constantly curved, but the two surfaces have a different radius of curvature. The figures illustrate the centre of curvature $C_1$, $C_2$ of the inferior surface and the superior surface of the intermediate portion of the laryngoscope, as well as the respective radii of curvature ($r_1$, $r_2$), distance of each centre of curvature from the centre line of the laryngoscope handle ($x_1$, $x_2$) which is positive in the same sense that the insertion section extends from the laryngoscope handle and negative in the opposite sense, and the distance of each centre of curvature from the laryngoscope insertion section ($y_1$, $y_2$).

The radius curvature of the inferior surface (n) is greater than the radius of curvature of the superior surface ($r_2$) in the intermediate portion of the insertion section. $y_1$, is also greater than $y_2$ and $x_2$ is greater than $x_1$. The insertion section is therefore thicker where it extends over a patient's palette. As a result of the relatively gradual curvature of the inferior surface, it is possible for a user to obtain both a direct view and an indirect view.

In a proximal portion of the insertion section, the curvature of the superior surface is continuous with the curvature of the superior surface in the intermediate portion. The superior surface may have the same centre of curvature in the proximal portion and the intermediate portion. However, the curvature of the inferior portion changes in the proximal portion and the inferior and superior surfaces both have the same centre of curvature, $C_2$, in the proximal portion. Thus, the insertion section is relatively thin where the blade is adjacent the patient's mouth, in contract to conventional blades which allow a direct view, such as the conventional Macintosh blade. Towards the distal end, the curvature of the superior surface changes further so that the insertion section narrows.

Further variations and modifications may be made within the scope of the invention herein disclosed.

The invention claimed is:

1. A laryngoscope blade comprising: a proximal portion, an intermediate portion, and a distal portion;
   a curved superior surface and a curved inferior surface each extending through the proximal, intermediate, and distal portions;
   a channel configured to receive a camera stick of a laryngoscope and extending from an opening at a proximal end of the laryngoscope blade and through at least part of the intermediate portion and terminating in a lens at a distal end of the channel, wherein the distal end of the channel is proximal to the distal portion of the laryngoscope blade, the channel being defined in part by an inferior internal surface of the laryngoscope blade, wherein the curvature of the inferior internal surface is greater than the curvature of the inferior surface of the intermediate portion; and
   an aperture disposed through the laryngoscope blade intermediate portion and between the inferior surface and a superior surface of the laryngoscope blade, wherein a proximal aperture terminus and a distal aperture terminus are positioned distally relative to the proximal end of the laryngoscope blade and proximally relative to the distal end of the channel.

2. The laryngoscope blade according to claim 1 wherein the distance between the inferior and superior surfaces is at a maximum within the intermediate portion.

3. The laryngoscope blade according to claim 1, wherein the curvature of the channel is substantially equal to the curvature of the superior surface.

4. The laryngoscope blade according to claim 1, wherein the curvature of the inferior surface at the intermediate and distal portions is less than the curvature of the inferior surface at a region between the intermediate and distal portions.

5. The laryngoscope blade according to claim 1, wherein the curvature of the inferior surface is defined by an inferior radius, and the curvature of the superior surface is defined by a superior radius, wherein the superior radius is smaller than the inferior radius.

6. The laryngoscope blade according to claim 1, wherein the curvature of the inferior surface is defined by an inferior radius, and the curvature of the inferior internal surface is defined by an internal radius, wherein the internal radius is smaller than the inferior radius.

7. The laryngoscope blade according to claim 1, wherein the aperture extends from a first lateral side surface to a second lateral side surface to extend through the laryngoscope blade.

8. The laryngoscope blade according to claim 7, wherein the aperture is elongate and has a superior inner surface substantially parallel to the inferior surface.

9. The laryngoscope blade according to claim 1, comprising a strengthening element disposed on or in at least a portion of the intermediate portion.

10. The laryngoscope blade according to claim 9, wherein the strengthening element extends within the distal portion.

11. The laryngoscope blade according to claim 9, wherein at least part of the strengthening element is planar and extends parallel to the superior surface of the intermediate section such that the strengthening element curves around at least a portion of the channel.

12. The laryngoscope blade according to claim 9, wherein at least part of the strengthening element extends between the inferior surface and the aperture.

13. The laryngoscope blade according to claim 9, wherein the strengthening element is a wire or filament composed of a secondary material which is strong in tension.

14. The laryngoscope blade according to claim 13, comprising a plurality of strengthening elements through the intermediate portion between the inferior surface and the aperture.

15. The laryngoscope blade according to claim 9, wherein the aperture extends through the strengthening element, between the inferior surface and the superior surface.

16. The laryngoscope blade according to claim 1, wherein a strengthening element extends along at least some of the length of the laryngoscope blade and a first portion of the strengthening element is generally parallel to the interior surface and a second portion of the strengthening element is generally perpendicular to the inferior surface, and wherein the first and second portions of the strengthening element meet along at least part of the length of the laryngoscope blade through which the strengthening element extends.

17. The laryngoscope blade according to claim 16, wherein a third portion of the strengthening element is generally parallel to the superior surface, and wherein the first and second portions, and the second and third portions, of the strengthening element meet along at least part of the length of the laryngoscope blade through which the strengthening element extends, the strengthening element thereby formed in the shape of a girder along at least part of the length of the laryngoscope blade.

18. The laryngoscope blade according to claim 1, wherein one or more of a camera, a light source, a light guide, a strengthening member, and an image capture device is provided in the channel.

19. The laryngoscope blade according to claim 1, further comprising a plurality of endotracheal tube guiding members extending laterally therefrom, having tube guiding surfaces which are arranged to contact and thereby guide the inferior or superior surface of a retained endotracheal tube introduced thereto.

20. The laryngoscope blade according to claim 1, wherein the inferior surface extends laterally beyond the superior surface along all or a substantial part of its length.

21. The laryngoscope blade according to claim 1, wherein the curvature of the superior surface of the proximal portion is the same or substantially the same as the curvature of the superior surface of the intermediate portion.

22. A laryngoscope, comprising:
a body portion; and
a laryngoscope blade comprising a proximal portion, an intermediate portion, a distal portion, and a channel extending along a length of the proximal portion and the intermediate portion and terminating in a lens proximal to a distal end of the laryngoscope blade; wherein the proximal portion of the laryngoscope blade is coupled to the body portion; and wherein the laryngoscope blade comprises an aperture disposed on an outer surface of the intermediate portion between the channel and an inferior surface of the laryngoscope blade, and wherein a curvature of an inner surface of the channel has a first curvature that is the same as a second curvature of a superior surface of the laryngoscope blade and is greater than a third curvature of an inferior surface of the laryngoscope blade.

23. The laryngoscope according to claim 22, wherein the laryngoscope blade comprises a resilient tab disposed on a proximal end of the proximal portion of the laryngoscope blade, wherein the resilient tab is configured to couple to the laryngoscope blade to the body portion of the laryngoscope such that the laryngoscope blade is releasably secured to the body portion.

24. The laryngoscope according to claim 23, comprising a camera stick extending from the body, wherein the camera stick is configured to be inserted into the channel of the laryngoscope blade.

25. The laryngoscope according to claim 24, wherein the camera stick is a strengthening member.

26. The laryngoscope according to claim 24, wherein the camera stick comprises one or more, or all, of; a camera, a light source, a light guide, a strengthening member, and an image capture device.

27. The laryngoscope according to claim 22, comprising a strengthening element disposed in at least the intermediate portion of the laryngoscope blade.

28. The laryngoscope according to claim 22, wherein the aperture extends through at lease a portion of a lateral side surface of the intermediate portion and wherein at least part of a strengthening element extends between the inferior surface and the aperture of the laryngoscope blade.

29. The laryngoscope according to claim 27, wherein the aperture extends through the intermediate portion, and through the strengthening element.

30. A kit comprising:
a laryngoscope body;
a camera stick extending from the laryngoscope body; and a laryngoscope blade configured to receive the camera stick and comprising a proximal portion, an intermediate portion, a distal portion, and a channel extending along a length of the proximal portion and the intermediate portion, wherein the channel terminates in a lens proximal to a distal end of the laryngoscope blade; wherein the channel is sized to receive the camera stick; and wherein the laryngoscope blade comprises an aperture disposed on an outer surface of the intermediate portion between the channel and an inferior surface of the laryngoscope blade.

31. The kit according to claim 30, wherein a distance between an inferior surface and a superior surface of the laryngoscope blade is at a maximum within the intermediate portion.

32. The kit according to claim 30, comprising a plurality of laryngoscope blades, wherein each laryngoscope blade of the plurality of laryngoscope blades comprises an inferior surface having a different curvature and a channel having an inferior internal surfaces with the same curvature relative to another laryngoscope blade of the plurality of laryngoscope blades.

33. The kit according to claim 30, comprising a plurality of laryngoscope blades, wherein each laryngoscope blade of the plurality of laryngoscope blades is a different size relative to another laryngoscope blade of the plurality of laryngoscope blades.

\* \* \* \* \*